United States Patent
Midha et al.

(10) Patent No.: US 9,326,922 B2
(45) Date of Patent: May 3, 2016

(54) ORAL CARE COMPOSITIONS CONTAINING HIGH PURITY BARIUM SULFATE PARTICLES

(71) Applicant: The Procter & Gamble Company, Cincinnati, OH (US)

(72) Inventors: Sanjeev Midha, Mason, OH (US); George Endel Deckner, Cincinnati, OH (US); Lawrence Edward Dolan, Cincinnati, OH (US); Eva Schneiderman, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/591,066

(22) Filed: Jan. 7, 2015

(65) Prior Publication Data

US 2015/0196470 A1    Jul. 16, 2015

Related U.S. Application Data

(60) Provisional application No. 61/927,494, filed on Jan. 15, 2014.

(51) Int. Cl.
*A61K 8/23* (2006.01)
*A61K 8/21* (2006.01)
*A61K 8/02* (2006.01)
*A61K 8/24* (2006.01)
*A61Q 11/00* (2006.01)

(52) U.S. Cl.
CPC .............. *A61K 8/23* (2013.01); *A61K 8/0241* (2013.01); *A61K 8/21* (2013.01); *A61K 8/24* (2013.01); *A61Q 11/00* (2013.01); *A61K 2800/412* (2013.01)

(58) Field of Classification Search
USPC ..................... 424/9.41, 50, 52, 333
See application file for complete search history.

(56) References Cited

U.S. PATENT DOCUMENTS

| | | | |
|---|---|---|---|
| 3,448,188 A * | 6/1969 | Hookman | 424/9.41 |
| 3,696,192 A | 10/1972 | Embring | |
| 3,699,221 A | 10/1972 | Schole et al. | |
| 3,988,433 A | 10/1976 | Benedict | |
| 4,108,979 A | 8/1978 | Muhler et al. | |
| 2007/0053849 A1 * | 3/2007 | Doyle et al. | 424/50 |
| 2014/0308321 A1 | 10/2014 | Midha et al. | |
| 2014/0308322 A1 | 10/2014 | Midha et al. | |

FOREIGN PATENT DOCUMENTS

GB         1261493      * 12/1972 ............... A61K 7/16

OTHER PUBLICATIONS

AIC "Barium Sulfate USP." Specification sheet: www.aicma.com;May 23, 2013.*
ExCalibar Minerals LLC: Barium Sulfate MSDS:ExBAR 200; Apr. 2008 www.excalibar.com.
PetroChemTrade, International Chemical Broker: Huberbrite, 2009.
Huberbrite Barium Sulfate Products, Quincy, IL: Huberbrite Barium Sulfate Products, Apr. 2010; www.hubermaterials.com.
Cimbar Performance Materials, BariScan Elite & Ultra Preliminary, Jan. 7, 2009; www.cimbar.com.

* cited by examiner

*Primary Examiner* — Walter Webb
(74) *Attorney, Agent, or Firm* — Alexandra S. Anoff

(57) ABSTRACT

Oral compositions containing high purity barium sulfate particles, preferably greater than 97.5% barium sulfate by weight of the particles, and an orally-acceptable carrier are effective for polishing or cleaning teeth and also exhibit enhanced fluoro compound and/or peroxide stability.

15 Claims, No Drawings

ORAL CARE COMPOSITIONS CONTAINING HIGH PURITY BARIUM SULFATE PARTICLES

FIELD OF THE INVENTION

The present invention relates to oral care compositions.

BACKGROUND OF THE INVENTION

Barium sulfate ($BaSO_4$), as a polishing agent, has been reported in sodium fluoride containing oral care (e.g., toothpaste) formulations. Fluoro compounds have long been used to reduce the incidence of dental caries. In order to prevent adsorption of the fluoro compounds by particles of barium sulfate, it has been reported to treat these particles with citric acid salts to suppress this absorption. Although the use of barium sulfate and fluoro compounds is generally reported, there is a continuing need to simplify formulations and processing steps to provide cost effective and efficacious toothpaste and other oral care formulations.

Peroxide has been included in oral care formulations for tooth whitening benefits. A problem with peroxide is the potential incompatibility with other formulation ingredients that can lead to pre-mature degradation of the peroxide leading to the release of oxygen. This released oxygen can lead to many undesirable consequences including: pressure buildup in a formulation dispensing container (that can lead to leaking or even bursting), inactivating the peroxide to render the formulation less efficacious for tooth whitening, or having the released oxygen undesirably react with other formulation ingredients. Although the use of barium sulfate and peroxide is generally reported, there is need to provide cost effective and efficacious toothpaste and other oral care formulations.

SUMMARY OF THE INVENTION

The present invention relates to oral care compositions comprising high purity barium sulfate particles, preferably greater than 97.5% of barium sulfate by weight of the particles. The present invention further relates to methods for cleaning and polishing dental enamel using these compositions.

Investigating different grades and types of $BaSO_4$ particles, it is surprisingly found that the purity of $BaSO_4$ affects the fluoride stability and its compatibility within tooth-paste compositions. In short, the more pure the particle of $BaSO_4$, the more fluoride stable and compatible the toothpaste. It is further surprising found that this stability and compatible is effected by rather slight differences in purity. ExBar 400 at 98.9% purity is more preferred than HB7 at 97.5%. In short, only 1.4% difference in purity makes material differences in fluoride stability and formulation compatibility. Without wishing to be bound by theory, the less pure grades of $BaSO_4$ particles contain higher levels of calcium carbonate and silica/silicates. It is believed these and other reactive chemical impurities can bind and/or influence the fluoride contained in the formulation to exert a negative impact to fluoride stability/compatibility.

It has also surprisingly found that the purity of $BaSO_4$ can affect peroxide stability and its compatibility in tooth-paste compositions. In short, the more pure the particle of $BaSO_4$, the more likely the peroxide is stable and compatible within a tooth-paste composition.

In one aspect of the invention, an oral care composition is provided comprising an effective amount of barium sulfate particles, wherein the particles comprise greater than 97.5% of barium sulfate by weight of the particles, preferably greater than 98%, alternatively greater than 98.5%, by weight of the particles; and an orally acceptable carrier.

In a second aspect of the invention, an oral care composition comprising an effective amount of particles of barium sulfate, wherein the particles are substantially free, preferably free, of an inorganic salt that contains a bivalent metal ion; and an orally acceptable carrier.

In yet another aspect of the invention, the above mentioned oral care compositions further comprise an effective amount of a fluoride ion source, preferably wherein the fluoride ion source is selected from sodium fluoride, or stannous fluoride, or mixtures thereof, preferably from 0.0025% to 2% of the fluoride ion source by weight of the oral care composition. In yet still another aspect of the invention, the above mentioned oral care compositions further comprise an effective amount of peroxide, preferably hydrogen peroxide, preferably from 0.1% to 10% of peroxide by weight of the oral care composition.

DETAILED DESCRIPTION OF THE INVENTION

The present invention therefore utilizes high purity barium sulfate particles in oral compositions, particularly in dentifrice compositions.

The present invention therefore relates to oral compositions containing, in a preferred embodiment, at least 0.01%, by weight of the composition, of high purity barium sulfate particles; and an orally acceptable carrier.

The term "high purity barium sulfate particles" means more than 97.5% barium sulfate by weight of the particles. Preferably the high purity barium sulfate particles means at least 98%, preferably at least 98.5%, more preferably at least 98.75%, even more preferably 98.9% barium sulfate by weight of the particles. Alternatively, greater than 99%, or 99.0%, or even 99.5% pure barium sulfate is used (by weight of the barium sulfate particles). Non-limiting examples of such high purity barium sulfate particles include those from ExCaliBar Minerals LLC (Houston, Tex., USA) on the trade name of ExBAR W Barytes™. Specific products names include ExBar W 325, ExBar W 400, ExBar W 4, ExBar W 2, and ExBar W 1. Median particles size in microns (when applicable) may include from 0.5 to 12, alternatively from 1 to 8, alternatively selected from the group consisting of 1, 2, 4, 8, or combinations thereof. A suitable instrument for measuring median particles size includes a HORIBA branded Laser Scattering Particle Size Distribution Analyzer Model La-910. In one embodiment, a percentage of those particles passing a 325 mesh may include at least 98, or 99.0, or 99.9, or 100 percent by weight. In another embodiment, the particles are free or substantially free of an inorganic salt that contains a bivalent metal ion, especially calcium carbonate and/or $Ca^{2+}$ and/or $Mg^{2+}$ cations. Without wishing to be bound by theory, the presence of bivalent cations may react undesirably with stannous fluoride or fluoride salts (e.g., sodium fluoride) contained in oral care compositions to form, for example, calcium fluoride ($Ca\ F_2$). Calcium fluoride is insoluble and reduced the anti-caries efficacy of fluoride. In yet another embodiment, the particles are free or substantially free of a magnesium salt and/or $Mg^{2+}$. Without wishing to be bound by theory, magnesium cations may interfere with fluoride solubility.

One example of barium sulfate particles that are specifically outside the scope of the present invention include those from Huber Engineered Material, J. M. Huber Corporation (Atlanta, Ga., USA) under the product name HUBER-BRITE™ Barium Sulfate products (Year: 2010), wherein the chemical analysis of these barium sulfate particles by weight percentage of the particles are: 97.5% barium sulfate; 1.6% calcium carbonate; 0.4% silica and silicates; 0.5% other (Year: 2010).

The present invention further relates to the above compositions wherein the composition comprises at least 0.01%, by weight of the composition, of an oral care active which may be selected from antibacterial agents, antiplaque agents, anticaries agents, antisensitivity agents, antierosion agents, oxidizing agents, anti-inflammatory agents, anticalculus agents, chelating agents, tooth substantive agents, antioxidants, analgesic agents, anesthetic agents, H-1 and H-2 antagonists, antiviral actives, nutrients and mixtures thereof or may be selected from stannous fluoride, sodium fluoride, monofluorophosphate, essential oils, mono alkyl phosphates, hydrogen peroxide, cetylpyridinium chloride, chlorhexidine, triclosan, and combinations thereof.

The present invention further relates methods of polishing tooth enamel, reducing plaque, gingivitis, sensitivity, oral malodor, erosion, cavities, calculus, inflammation, and staining by administering to a subject's oral cavity one or more of the above compositions.

While the specification concludes with claims that particularly point out and distinctly claim the invention, it is believed the present invention will be better understood from the following description.

Definitions

The term "orally acceptable carrier" as used herein means a suitable vehicle or ingredient, which can be used to form and/or apply the present compositions to the oral cavity in a safe and effective manner.

The term "comprising" as used herein means that steps and ingredients other than those specifically mentioned can be added. This term encompasses the terms "consisting of" and "consisting essentially of." The compositions of the present invention can comprise, consist of, and consist essentially of the essential elements and limitations of the invention described herein, as well as any of the additional or optional ingredients, components, steps, or limitations described herein.

The term "effective amount" as used herein means an amount of a compound or composition sufficient to induce a positive benefit, an oral health benefit, and/or an amount low enough to avoid serious side effects, i.e., to provide a reasonable benefit to risk ratio, within the sound judgment of a skilled artisan. In one embodiment, "effective amount" means at least 0.01% of the material, by weight of the composition, alternatively at least 0.1%.

The term "oral composition" as used herein means a product that in the ordinary course of usage is retained in the oral cavity for a time sufficient to contact some or all of the dental surfaces and/or oral tissues for purposes of oral activity. In one embodiment, the composition is an "oral care composition" meaning that the composition provides a benefit when used in the oral cavity. The oral composition of the present invention may be in various forms including toothpaste, dentifrice, tooth gel, tooth powders, tablets, rinse, sub gingival gel, foam, mouse, chewing gum, lipstick, sponge, floss, prophy paste, petrolatum gel, or denture product. In one embodiment, the oral composition is in the form of a paste or gel. In another embodiment, the oral composition is in the form of a dentifrice. The oral composition may also be incorporated onto strips or films for direct application or attachment to oral surfaces, or incorporated into floss.

The term "dentifrice" as used herein means paste, gel, powder, tablets, or liquid formulations, unless otherwise specified, that are used to clean the surfaces of the oral cavity.

The term "teeth" as used herein refers to natural teeth as well as artificial teeth or dental prosthesis.

The term "polymer" as used herein shall include materials whether made by polymerization of one type of monomer or made by two (i.e., copolymers) or more types of monomers. The term "water soluble" as used herein means that the material is soluble in water in the present composition. In general, the material should be soluble at 25° C. at a concentration of 0.1% by weight of the water solvent, preferably at 1%, more preferably at 5%, more preferably at 15%.

The term "phase" as used herein means a mechanically separate, homogeneous part of a heterogeneous system.

The term "majority" as used herein means the greater number or part, a number more than half the total. The term "median" as used herein means the middle value in a distribution, above and below which lie an equal number of values.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. The term "weight percent" may be denoted as "wt %" herein. All molecular weights as used herein are weight average molecular weights expressed as grams/mole, unless otherwise specified.

High Purity Barium Sulfate Particles

The oral compositions herein contain an effective amount of high purity barium sulfate particles to provide an abrasive, tooth-cleaning or polishing benefit. The oral compositions herein may include from about 0.1% to about 30%, by weight of the composition, of the particles. In another embodiment, the composition comprises from about 0.5% to about 20%, by weight of the composition, alternatively from about 1% to about 10%, by weight of the composition, of the particles. The composition may include from about 0.1% to about 50%, alternatively from about 1% to about 40%, alternatively from about 2% to about 35%, alternatively from about 4% to about 30%, alternatively from about 5% to about 25%, by weight of the composition, alternatively combinations thereof, of the high purity barium sulfate particles.

Tables 1A and 1B show the published properties of ExBAR W Barytes materials available from ExCaliBar Minerals, LLC (Houston, Tex.). See www.excalibar.com.

TABLE 1A

Physical Properties of ExBAR ™ materials:
Typical Physical Properties

|  | ExBAR W 325 | ExBAR W 400 | ExBAR W 4 | ExBAR W 2 | ExBAR W 1 |
| --- | --- | --- | --- | --- | --- |
| Color* | 95 | 96 | 96 | 96 | 96 |
| % Passing 325 Mesh | 98.0 | 99.9 | 100 | 100 | 100 |
| Median Particle Size, μ | N/A | 8 | 4 | 2 | 1 |
| Top Size, μ | 40 | 35 | 15 | 12 | 8 |
| Specific Gravity | 4.4 | 4.4 | 4.4 | 4.4 | 4.4 |
| pH | 7.6 | 7.6 | 7.6 | 7.6 | 7.6 |
| Moisture | 0.1 | 0.1 | 0.1 | 0.1 | 0.1 |
| Oil**Absorption | 9 | 10 | 12 | 13 | 15 |
| Loose | 99 | 90 | 75 | 60 | 55 |
| Packed | 140 | 130 | 120 | 105 | 95 |

*Hunter Dry Brightness, L Value
**Spatula Rubout Method

TABLE 1B

Chemical Analysis of ExBAR W Barytes:

| Parameter | Exbar 400 | Huberbrite 7 |
|---|---|---|
| BaSO4 | 98.9% | 97.5% |
| SrSO4 | 0.6% | |
| FeO3 | 0.007% | |
| SiO2 | 0.36% | 0.4% |
| CaO | 0.05% | |
| Al2O3 | <0.005% | |
| CaCO3 | | 1.6% |
| Others | | 0.5% |

Table 2 shows the published properties of BariScan Elite and BariScan Ultra materials available from Cimbar Performance Minerals (Cartersville, Ga.). See www.cimbar.com.

TABLE 2

Physical Properties of BariScan Elite & Ultra ™ materials:

| Product Name: | BariScan Elite | BariScan Ultra |
|---|---|---|
| % Barium Sulfate | 98 | 98 |
| Median Particle Size: Microns | 1 | 10 |
| Top size: Microns | 12 | 40 |
| % Passing - 325 Mesh Screen | 100% | 99.5% |
| pH approximately | 5 | 5 |
| Hegman Fineness | 7.0 | 4.5 |
| Specific Gravity | 4.4 | 4.4 |
| Whiteness (L) % | 96 | 95 |

In one embodiment, the high purity barium sulfate particles of the present invention, further comprises one or more of the following ingredients totaling less than 2.5 wt % of the particles, preferably less than 2 wt %, more preferably less than 1.5 wt %, alternatively from 0.01% to 1.1% by weight of the particles: $SrSO_4$; $Fe2O_3$; $SiO_2$; CaO, $AL_2O_3$; and combinations thereof.

In another embodiment, the high purity barium sulfate particles of the present invention comprise less than 1.6% of calcium carbonate by weight of the particles, preferably less than 1 wt %, more preferably less than 0.5 wt %, yet even more preferably are free or substantially free of calcium carbonate.

In yet another embodiment, the high purity barium sulfate particles of the present invention comprise less than 0.4% of silica and silicates by weight of the particles, alternatively less than 0.1 wt % of silica and silicates, alternatively free or substantially free of silica and silicates.

In yet another embodiment, the high purity barium sulfate particles of the present invention meet or exceed the requirements for barium sulfate of the United States Pharmacopeia (USP) and/or European Pharmacopeia (EP).

Oral Care Active

One of the advantages of high purity barium sulfate particles is its compatibility with other materials, particularly materials that are reactive and can lose efficacy such as some oral care actives. Because surprisingly, high purity barium sulfate particles do not react as much as less pure forms of barium sulfate particles, less of the active can be used with the same efficacy. If the oral care active has any potential aesthetic negatives such an unpleasant or strong taste, astringency, staining, or other negative aesthetic, the lower amount of active may be preferred. Additionally, the use of less active for the same or similar efficacy is a cost savings. Alternatively, if the same amount of active as used as traditionally used, the active would have higher efficacy as more of it is available to provide the benefit.

Oral care actives useful herein include antibacterial agents, antiplaque agents, anticaries agents, antisensitivity agents, antierosion agents, oxidizing agents, anti-inflammatory agents, anticalculus agents, chelating agents, tooth substantive agents, antioxidants, analgesic agents, anesthetic agents, H-1 and H-2 antagonists, antiviral actives, nutrients and mixtures thereof. These materials are described more fully below and a material or ingredient may be categorized as more than one type of materials. Such as an antioxidant may also be an antiplaque and antibacterial active. Examples of suitable actives include stannous fluoride, sodium fluoride, essential oils, mono alkyl phosphates, hydrogen peroxide, CPC, chlorhexidine, Triclosan, and combinations thereof.

In one embodiment, the oral care active is selected from stannous fluoride, sodium fluoride, monofluorophosphate, cetylpyridinium chloride, triclosan, arginine, and mixtures thereof. Mixtures of oral care actives may be used. In one embodiment, the oral care active is selected from one or more of a fluoride ion source, zinc ion source, calcium ion source, phosphate ion source, potassium ion source, strontium ion source, aluminum ion source, magnesium ion source, or combinations thereof. In one embodiment, the oral care active is a mixture of stannous ion source, fluoride ion source, and zinc ion source.

In another embodiment, the oral care active is peroxide. Preferably the peroxide is selected from the group consisting of hydrogen peroxide, calcium peroxide, sodium peroxide, carbamide peroxide, urea peroxide, sodium percarbonate, and mixtures thereof; more preferably the peroxide is hydrogen peroxide. An effective amount of peroxide is preferably incorporated in the oral care composition. In one embodiment, the oral care composition comprises from 0.01% to 10% of peroxide by weight of the oral care composition; preferably 0.1% to 10%, alternatively from 0.2% to 8%, or from 0.5% to 5%, or from 1% to 3%, or from 2% to 6%, or from 3% to 7%, or from 1% to 3%, or combinations thereof, of peroxide by weight of the oral care composition.

Antibacterial Agent

The oral care active may include an effective amount of an antibacterial agent. The composition may contain from about 0.001% to about 20%, alternatively from about from about 0.1% to about 5%, by weight of the oral care composition, of one or more antibacterial agents. Non-limiting examples may include those described in US 2012/0082630 A1 paragraphs 53 and 54, and the references cited therein.

Anti-Plaque Agent

The oral care active may include an effective amount of an anti-plaque agent or anti-tartar agent. The composition may contain from about 0.001% to about 20%, alternatively from about from about 0.1% to about 5%, by weight of the oral care composition, of one or more anti-plaque agents. Non-limiting examples include pyrophosphate salt as a source of pyrophosphate ion. See other non-limiting examples of anti-tartar agents at US 2012/0082630 A1, paragraph 55.

Anti-Caries Agent

The oral care active may include an effective amount of an anti-caries agent. In one embodiment, the anti-caries agent is a fluoride ion source. The fluoride ion may be present in an amount sufficient to give a fluoride ion concentration in the composition at 25° C., and/or in one embodiment can be used at levels of from about 0.0025% to about 5% by weight of the composition, alternatively from about 0.005% to about 2.0% by weight of the composition, to provide anti-caries effectiveness. Examples of suitable fluoride ion-yielding materials are disclosed in U.S. Pat. Nos. 3,535,421, and 3,678,154. Representative fluoride ion sources include: stannous fluoride, sodium fluoride, potassium fluoride, amine fluoride, sodium monofluorophosphate, zinc fluoride, and mixtures thereof. In one embodiment the oral care composition contains a fluoride source selected from stannous fluoride, sodium fluoride, and mixtures thereof.

pH

The pH of the oral composition may be from about 3 to about 10. The pH is typically measured as a slurry pH by methods known in the industry. Depending upon the actives used in the oral composition, a different pH may be desired. For formulations containing Stannous Fluoride, it may be desired to have a pH slightly lower than typical dentifrices. Compositions containing of high purity barium sulfate particles and fluoride may have a pH of less than about 6.5 or less than about 5.5. The pH may be less than about 5.2 or about 5.0. It may be desired to have a pH of from about 3.5 to about 5 or from about 2.4 to about 4.8. For formulations containing peroxide and of high purity barium sulfate particles, the pH may be less than 5.5, alternatively less than 5.0, alternatively less than 4.5. A formulation with peroxide and of high purity barium sulfate particles may be from about 3.5 to about 4.0. For formulations comprising of high purity barium sulfate particles, stannous, and fluoride, it may be desired to have a pH of less than 5.0. Without being limited by theory, a pH of less than 5.0 may enable more of the $SnF_3$ stannous species to be formed.

Anti-Sensitivity Agent

The oral care active may include an effective amount of an anti-sensitivity agent. The composition may contain from about 0.001% to about 20%, alternatively from about from about 0.1% to about 5%, by weight of the oral care composition, of the anti-sensitivity agent. Non-limiting examples include those described in US 2012/0052022 A1 at paragraph 41, and US 2009/0311200 A1 at paragraph 59.

Anti-Erosion Agent

The oral care active may include an effective amount of an anti-erosion agent, such as a stannous ion source. As stated before, one of the advantages of high purity barium sulfate particles is its compatibility with other materials, particularly materials that are reactive and can lose efficacy, such as stannous ions. Because of high purity barium sulfate particles do not react as much with stannous as compared to precipitated silica and other traditional abrasives, less of the stannous can be used with the same efficacy. It has been reported that stannous may have potential aesthetic negatives such an unpleasant or strong taste, astringency, staining, or other negative aesthetics that make the stannous containing oral compositions less desirable for consumers.

The stannous ions may be provided from stannous fluoride and/or other stannous salts. Stannous fluoride has been found to help in the reduction of gingivitis, plaque, sensitivity, erosion, and in improved breath benefits. Formulations providing such efficacy typically include stannous levels provided by stannous fluoride and/or other stannous salts ranging from about 50 ppm to about 15,000 ppm stannous ions in the total composition. The stannous ion is present in an amount of from about 1,000 ppm to about 10,000 ppm, in one embodiment from about 3,000 ppm to about 7,500 ppm. Other stannous salts include organic stannous carboxylates, such as stannous acetate, stannous gluconate, stannous oxalate, stannous malonate, stannous citrate, stannous ethylene glycoxide, stannous formate, stannous sulfate, stannous lactate, stannous tartrate, and the like. Other stannous ion sources include stannous halides such as stannous chlorides, stannous bromide, stannous iodide and stannous chloride dihydrate. In one embodiment the stannous ion source is stannous fluoride, in another embodiment stannous chloride dehydrate or trihydrate, or stannous gluconate. The combined stannous salts may be present in an amount of from about 0.001% to about 11%, by weight of the oral care compositions. The stannous salts may, in one embodiment, be present in an amount of from about 0.01% to about 7%, in another embodiment from about 0.1% to about 5%, and in another embodiment from about 1.5% to about 3%, by weight of the oral care composition.

Whitening and Oxidizing Agent

The oral care active may include an effective amount of whitening or oxidizing agent. Non-limiting examples include those described in US 2012/0082630 A1 at paragraph 56.

Anti-Inflammatory Agent

The oral care active may include an effective amount of an anti-inflammatory agent. Non-limiting examples include those described in US 2011/0104081 A1 at paragraph 55.

Anticalculus Agent

The oral care active may include an effective amount of an anti-calculus agent, which in one embodiment may be present from about 0.05% to about 50%, by weight of the oral care composition, alternatively from about 0.05% to about 25%, alternatively from about 0.1% to about 15%. Non-limiting examples include those described in US 2011/0104081 A1 at paragraph 64, and those described in US 2012/0014883 A1 at paragraphs 63 to 68, as well as the references cited therein.

Chelating Agent

The oral care active may include an effective amount of a chelating agent, also referred to as sequestrants, many of which also have anticalculus activity or tooth substantive activity. Use of chelating agents in oral care products is advantageous for their ability to complex calcium such as found in the cell walls of bacteria, to disrupt plaque and to complex with metallic ions. Chelation of ions, such as iron or copper, helps retard oxidative deterioration of finished products. Non-limiting examples of chelating agents include those described in US 2011/0020246 A1 at paragraphs 21-28.

Tooth Substantive Agent

The oral care active may include an effective amount of a tooth substantive agent. For purposes of this application, tooth substantive agents are included as chelants also. Suitable agents may be polymeric surface active agents (PMSA's), including polyelectrolytes, more specifically anionic polymers. Non-limiting examples include those described in US 2012/0014883 A1 at paragraphs 74 to 84, and the references cited therein.

Analgesic and Anesthetic Agent

The oral care active may include an effective amount of an anti-pain or desensitizing agent. Non-limiting examples include those described in US 2008/0081023 A1 at paragraph 117, and the reference cited therein.

H-1 and H-2 Antagonist and Antiviral Active

The oral care active may include an effective amount of a selective H-1 and H-2 antagonist including a compound disclosed in U.S. Pat. No. 5,294,433. The stannous salts that may be used in the present invention would include organic stannous carboxylates and inorganic stannous halides. While stannous fluoride may be used, it is typically used only in combination with another stannous halide or one or more stannous carboxylates or another therapeutic agent.

Nutrient

The oral care active may include an effective amount of a nutrient. Nutrients include minerals, vitamins, oral nutritional supplements, enteral nutritional supplements, and mixtures thereof. Non-limiting examples include those described in US 2008/0081023 A1 at paragraph 115, and the reference cited therein.

Additional Active

An additional active suitable for use in the present invention may include, but are not limited to, insulin, a steroid, and herbal and other plant derived remedies. Additionally, an anti-gingivitis or gum care agent may also be included. A component imparting a clean feel to teeth may optionally be included. These components may include, for example, baking soda or Glass-H. Combinations of the materials listed above may be used, for instance, an anti-microbial and an anti-inflammatory agent may be combined in a single dentifrice composition to provide combined effectiveness.

Surfactant

The compositions herein may include a surfactant. The surfactant may be selected from anionic, nonionic, amphoteric, zwitterionic, cationic surfactants, or mixtures thereof. The oral care composition may include a surfactant at a level of from about 0.1% to about 50%, from about 0.025% to about 9%, from about 0.05% to about 5%, from about 0.1% to about 2.5%, from about 0.5% to about 2%, or from about 0.1% to about 1% by weight of the total composition. Non-limiting examples of anionic surfactants may include those described at US 2012/0082630 A1 at paragraphs 32, 33, 34, and 35. Non-limiting examples of zwitterionic or amphoteric surfactants may include those described at US 2012/0082630 A1 at paragraphs 36; cationic surfactants may include those described at paragraphs 37; and nonionic surfactants may include those described at paragraph 38.

Orally-Acceptable Carrier

The carrier for the components of the present compositions may be any orally-acceptable vehicle suitable for use in the oral cavity. The orally-acceptable carrier includes materials such as buffering agents, secondary abrasive materials, alkali metal bicarbonate salts, thickening agents, gel networks, humectants, water, surfactants, titanium dioxide, flavor agents, coolants, sweetening agents, coloring agents, other suitable materials, and mixtures thereof. The composition may include from about 0.001% to about 90%, alternatively from about 0.01% to about 50%, alternatively from about 0.1% to about 30%, by weight of the oral care composition, of the orally acceptable carrier.

Buffering Agent

The oral care compositions herein may include an effective amount of a buffering agent. Buffering agents, as used herein, refer to agents that can be used to adjust the pH of the dentifrice compositions to a range of about pH 3.0 to about pH 10. The buffering agents include alkali metal hydroxides, ammonium hydroxide, organic ammonium compounds, carbonates, sesquicarbonates, borates, silicates, phosphates, imidazole, and mixtures thereof. Specific buffering agents include monosodium phosphate, trisodium phosphate, sodium benzoate, benzoic acid, sodium hydroxide, potassium hydroxide, alkali metal carbonate salts, sodium carbonate, imidazole, pyrophosphate salts, sodium gluconate, lactic acid, sodium lactate, citric acid, sodium citrate, phosphoric acid.

Secondary Abrasive

The oral care compositions herein may further include from about 0.1% to about 60%, alternatively from about 1% to about 50%, alternatively from about 2% to about 40%, alternatively from about 4% to about 30%, alternatively from about 5% to about 25%, by weight of the composition, of one or more secondary abrasives or mixtures thereof. Examples of secondary abrasive materials useful herein include, precipitated silica, fused silica, calcium carbonate, dicalcium phosphate dihydrate, phosphates (including orthophosphates), pyrophosphates, perlite, pumice, nanodiamonds, surface treated and de-hydrated precipitated silica, rice hull silica, silica gels, aluminas, polymetaphosphates, other inorganic particulates, and mixtures thereof. Examples of secondary abrasive materials useful herein include dicalcium orthophosphate dihydrate, calcium pyrophosphate, tricalcium phosphate, calcium polymetaphosphate, insoluble sodium polymetaphosphate, hydrated alumina, beta calcium pyrophosphate, calcium carbonate, and resinous abrasive materials such as particulate condensation products of urea and formaldehyde, and others such as disclosed in U.S. Pat. No. 3,070,510. In one embodiment, the composition includes from about 2% to about 40%, alternatively from about 3% to about 30%, by weight of the composition, of high purity barium sulfate particles and from about 2% to about 40%, alternatively from about 3% to about 30%, by weight of the composition, of a secondary abrasive.

In one embodiment, the composition includes from about 2% to about 40%, alternatively from about 3% to about 30%, by weight of the composition, of high purity barium sulfate particles and from about 2% to about 40%, alternatively from about 3% to about 30%, by weight of the composition, of a secondary abrasive. In one embodiment, the secondary abrasive is selected from precipitated silica, calcium pyrophosphate, and mixtures thereof.

Thickening Agent

The oral care compositions herein may include one or more thickening agents, such as a polymeric thickener. A thickening agent may be used in an amount from about 0% to about 15%, or from about 0.01% to about 10%, or from about 0.1% to about 5%, by weight of the total oral composition. Non-limiting examples include those described in US 2008/0081023 A1 at paragraphs 134 to 137, and the references cited therein.

Gel Network

The oral care compositions herein may include a gel network. Gel networks useful in oral care compositions are described in more detail in U.S. Pat. No. 8,216,552 and US Patent Publications, 2008/0081023 and 2009/0246151. The gel network may include a fatty amphiphile, surfactant, and a solvent. In one embodiment, the composition includes a gel network and contains from about 0.05% to about 30%, alternatively from about 0.1% to about 20%, alternatively from about 0.5% to about 10%, by weight of the oral composition of a fatty amphiphile; from about 0.01% to about 15%, alternatively from about 0.1% to about 10%, alternatively from about 0.3% to about 5%, by weight of the oral composition, of the surfactant; and at least about 0.05% of a solvent, alternatively from about 0.1% to about 99%, from about 0.5% to about 95%, or from about 1% to about 90%, by weight of the composition, of the solvent.

In one embodiment, the fatty amphiphile is selected from cetyl alcohol, stearyl alcohol, and mixtures thereof. In one embodiment, the surfactant is selected from anionic, zwitterionic, amphoteric, cationic, and nonionic surfactants. In one embodiment, anionic surfactants such as sodium lauryl sulfate are preferred. Suitable solvents for the present invention include water, edible polyhydric alcohols such as glycerin, diglycerin, triglycerin, sorbitol, xylitol, butylene glycol, erythritol, polyethylene glycol, propylene glycol, and combinations thereof. In one embodiment, the solvent is selected from sorbitol, glycerin, water, and combinations thereof.

Humectant

The compositions herein may include from about 0.1% to about 99%, from about 0.5% to about 95%, or from about 1% to about 90%, by weight of the composition, of a humectant. Suitable humectants for the present invention include water, edible polyhydric alcohols such as glycerin, sorbitol, xylitol, butylene glycol, polyethylene glycol, propylene glycol, and combinations thereof. In one embodiment, the humectant is selected from sorbitol, glycerin, water, and combinations thereof.

Water

The compositions herein may include from about 10% to about 99%, by weight of the composition of water. In one embodiment, the composition includes from about 30% to about 80%, alternatively from about 30% to about 70%, alternatively from about 30% to about 50%, by weight of the composition, of water. In one embodiment, the composition includes less than 20% water.

Flavoring Agents and Sensates

The compositions herein may include from about 0.001% to about 5%, alternatively from about 0.01% to about 4%, alternatively from about 0.1% to about 3%, alternatively from about 0.5% to about 2%, by weight of the oral care composition, of a flavoring agent or sensate, or combinations thereof. Flavoring agent may include those described in US 2012/0082630 A1 at paragraph 39; and sensates (e.g., coolants, warming sensates, and tingling sensates) may include those described at paragraphs 40-45.

Sweetener

The oral care compositions herein may include a sweetening agent. These include sweeteners such as saccharin, dextrose, sucrose, lactose, xylitol, maltose, levulose, aspartame, sodium cyclamate, D-tryptophan, dihydrochalcones, acesulfame, sucralose, neotame, and mixtures thereof. Sweetening agents are generally used in oral compositions at levels of from about 0.005% to about 5%, by weight of the composition. See also US 2012/0082630 A1, esp. paragraphs 21 to 28.

Coloring Agents

The oral care compositions herein may include a coloring agent. The coloring agent may be in the form of an aqueous solution, preferably 1% coloring agent in a solution of water. Pigments, pealing agents, filler powders, talc, mica, magnesium carbonate, calcium carbonate, bismuth oxychloride, zinc oxide, and other materials capable of creating a visual change to the dentifrice compositions may also be used. Color solutions and other agents generally comprise from about 0.01% to about 5%, by weight of the composition. Titanium dioxide may also be added to the present composition. Titanium dioxide is a white powder which adds opacity to the compositions. Titanium dioxide generally comprises from about 0.25% to about 5%, by weight of the composition.

The composition may be essentially free of surfactant, fluoride, and/or any one or more oral care actives. In one embodiment, the compositions herein are free of one or more of the following: enzymes, colorant particles, solvents capable of solubilizing the high purity barium sulfate particles, colorant particles, and/or triclosan.

Method of Use

The present invention also relates to methods for cleaning and polishing teeth. The method of use herein comprises contacting a subject's dental enamel surfaces and oral mucosa with the oral compositions according to the present invention. The method of treatment may be by brushing with a dentifrice or rinsing with a dentifrice slurry or mouthrinse. Other methods include contacting the topical oral gel, mouthspray, toothpaste, dentifrice, tooth gel, tooth powders, tablets, subgingival gel, foam, mouse, chewing gum, lipstick, sponge, floss, petrolatum gel, or denture product or other form with the subject's teeth and oral mucosa. Depending on the embodiment, the oral composition may be used as frequently as toothpaste, or may be used less often, for example, weekly, or used by a professional in the form of a prophy paste or other intensive treatment.

EXAMPLES

The following examples and descriptions further clarify embodiments within the scope of the present invention. These examples are given solely for the purpose of illustration and are not to be construed as limitations of the present invention as many variations thereof are possible without departing from the spirit and scope.

Examples 1-4 are dentifrice compositions that may be suitably prepared by conventional methods chosen by the formulator. Examples 1 and 3 are inventive formulations while examples 2 and 4 are comparative examples to illustrate one or more advantages of those inventive formulations containing high purity barium sulfate particles. Specifically, examples 1 and 3 contain ExBar W4 barium sulfate particles (98.9% barium sulfate by weight of particles) while examples 2 and 4 contain HUBERBRITE 7 (HB 7) barium sulfate particles (97.5% barium sulfate by weight of particles). Notably examples 1 and 2 contain stannous fluoride, and examples 3 and 4 contain sodium fluoride (i.e., are stannous free).

TABLE 3

Formulations of examples 1 and 2.

| Material (wt %) | Example 1 (Inventive) | Example 2 (Comparative) |
|---|---|---|
| Purified Water | 25.200% | 25.200% |
| Sorbitol (Archer Daniels Midland) | 37.632% | 37.632% |
| ExBAR 400 (98.9 wt % of barium sulfate) | 15.000% | 0 |
| HUBERITE 7 (97.5 wt % of barium sulfate) | 0 | 15.000% |
| GANTREZ S-95 35 wt % Solution (ISP Tech.) | 5.710% | 5.710% |
| Sodium Lauryl Sulfate 28 wt % Solution (Stepan) | 5.000% | 5.000% |
| Xylitol (Danisco) | 3.000% | 3.000% |
| Flavor | 1.200% | 1.200% |
| Sodium Gluconate (PMP Fermentation Products) | 1.064% | 1.064% |
| CARRAGEENAN MIXTURE IOTA SILICA ADD (FMC Corporation) | 1.080% | 1.080% |
| Zinc Lactate (Jost Chemical) | 1.000% | 1.000% |
| Hydroxyethyl Cellulose 250M (Asland Indust.) | 0.720% | 0.720% |
| Sodium Saccharin (High Trans Corp.) | 0.800% | 0.800% |
| Xanthan Gum (CP Kelco) | 0.540% | 0.540% |
| Stannous Fluoride (Stella Chemifa) | 0.454% | 0.454% |
| Sodium Hydroxide (PPG Industries Inc.) | 1.400% | 1.400% |
| Dye, FD&C Blue #1 Color Solution, Non-Alcohol (Procter & Gamble) | 0.200% | 0.200% |
| Total: | 100.000% | 100.000% |
| Target pH: | 5.6 | 5.6 |

TABLE 4

Tin Compatibility with Barium Sulfate

| Days at 40° C. | Example 1 (Inventive) | Example 2 (Comparative) |
|---|---|---|
| 0 | 100% | 100% |
| 30 | 85% | 94% |
| 60 | 94% | 93% |
| 90 | 98% | 90% |

TABLE 5

Fluoride Stability with Barium Sulfate

| Days at 40° C. | Example 1 (Inventive) | Example 2 (Comparative) |
|---|---|---|
| 0 | 99% | 83% |
| 30 | 100% | 64% |
| 60 | 100% | 61% |
| 90 | 100% | 58% |

Table 4 assesses tin compatibility of stannous fluoride containing formulations by comparing the inventive composition example 1 and comparative composition example 2 over the course of 90 days at 40° C. Specifically, tin stability is assessed at days 30, 60, and 90 while the compositions are subjected to 40° C. Stannous fluoride is also referred to as Tin (II) fluoride ($SnF_2$). Stannous fluoride converts the calcium mineral apatite into fluoroapetite, which makes tooth enamel more resistant to bacteria-generated acid attacks. To assess the compatibility of barium sulfate particles with stannous fluoride, compatibility is assessed with both the tin portion of the stannous fluoride (in Table 4) and the fluoride portion (in Table 5). Incompatibility with tin is demonstrated by ion chromatography. Gas Chromatography/Mass Spectrometry are used to assess the amount of tin at 30, 60, and 90 days while the compositions are subjected to 40° C. temperature. Barium sulfate particles demonstrate little to no tin incompatibility vs. theoretical. At day 90, inventive example 1 shows 8% higher tin stability than comparative example 2. Stannous compatibility is determined by the measurement of available tin vs. theoretical using ion chromatography.

Similarly Table 5 assesses the fluoride stability of the stannous fluoride containing composition of example 1 and 2. Fluoride stability is assessed at days 30, 60, and 90 while the compositions are subjected to 40° C. Incompatibility with fluoride is demonstrated by ion chromatography. Gas Chromatography/Mass Spectrometry are used to assess the amount of tin at 30, 60, and 90 days while the compositions are subjected to 40° C. temperature. Barium sulfate particles demonstrate little to no fluoride incompatibility vs. theoretical. At day 90, inventive example 1 shows 42% higher fluoride stability than comparative example 2.

TABLE 6

Examples 3 and 4 are stannous-free dentifrice compositions of inventive and comparative compositions, respectively.

| Material (wt %) | Example 3 (Inventive) | Example 4 (Comparative) |
|---|---|---|
| Sorbitol (Sorbitol Solution USP, Archer Daniels Midland) | 65.522% | 65.522% |
| ExBAR 400 (98.9% of barium sulfate) | 15.000% | 0 |
| HUBERITE 7 (97.5% of barium sulfate) | 0 | 15.000% |
| Purified Water | 11.165% | 11.165% |
| Sodium Lauryl Sulfate 28 wt % solution (Stepan Co) | 4.000% | 4.000% |
| Flavor | 0.900% | 0.900% |
| Cellulose Gum | 0.700% | 0.700% |
| Trisodium Phosphate (ICL Performance Products) | 1.450% | 1.450% |
| Sodium Phosphate (ICL Performance Products) | 0.590% | 0.590% |
| CARBOMER (Lubrizol Advanced Materials) | 0.300% | 0.300% |
| Sodium Fluoride (Sunlit Fluo Chemical Company) | 0.243% | 0.243% |
| Sodium Saccharin (High Trans Corp.) | 0.130% | 0.130% |
| Total: | 100% | 100% |
| Target pH | 7.0 | 7.0 |

TABLE 7

Fluoride Stability in a Stannous Free Chassis

| Days at 40° C. | Example 3 (Inventive) | Example 4 (Comparative) |
|---|---|---|
| 0 | 93% | 37% |
| 30 | 88% | 27% |
| 60 | 87% | 27% |
| 90 | 88% | 27% |

Table 7 illustrates higher fluoride stability in inventive composition of Example 3 containing high purity barium sulfate particles compared to comparative Example 4. Fluoride stability is assessed at days 30, 60, and 90 while the compositions are subjected to 40° C. Incompatibility with fluoride is demonstrated by ion chromatography by exhibiting only 12% degradation of fluoride as compared to the comparative example that exhibited 73% degradation of fluoride.

Turing to Tables 8A and 8B, Formulations A and B each containing 15 wt % of high purity barium sulfate particles and are both tested for hydrogen peroxide degradation over two weeks while heated at 50° C. Components of Formulas A and B are detailed in Table 8B herein below.

TABLE 8A

Peroxide Stability in at 50° C. Over Two Weeks

| Formulation: | % $H_2O_2$ Initial Week Average | % $H_2O_2$ Two Week Average |
|---|---|---|
| A. 15% $BaSO_4$ (Bariscan Ultra) | 3.02 (3.02, 3.02) | 2.98 (2.97, 2.98) |
| B. 15% $BaSO_4$ (Bariscan Ultra, acid washed) | 3.07 (3.06, 3.07) | 3.06 (3.15, 2.97) |

Heating was used to hasten any peroxide degradation effects. Formulation A contains Bariscan Ultra™ branded barium sulfate particles, while Formula B contains Barisan Ultra™ acid washed particles branded barium sulfate particles. Both of these barium sulfate particles are available from Cimbar Performance Minerals, Cartersville, Ga. and most notably are both at 98 wt % purity of barium sulfate. As is indicated in Table 8A, the initial week average (of a sample size of two for each formulation) indicate a 3.02 wt % of hydrogen peroxide for formula A and 3.07 wt % hydrogen peroxide for formula B. After two weeks, the percentage of hydrogen peroxide remains virtually unchanged at average value of 2.98 wt % and 3.06 wt % for formulations A and B, respectively. This demonstrates that high purity barium sulfate particles will not materially cause any degradation of hydrogen peroxide over time and heated conditions.

TABLE 8B

Components of Formulations A and B.

| Material (Wt %) | Formula A | Formula B |
|---|---|---|
| Lanette ® W (Cetyl alcohol/stearyl alcohol/sodium lauryl sulfate (BASF)) | 14 | 14 |
| SLS Powder (Sodium Lautyl Sulfate, Stephan) | 1.750 | 1.750 |
| Water | 59.25 | 57.996 |
| Partial Total: | 73.746 | 73.746 |
| Barium Sulfate (C-325 CIMBAR) | 15 | 0 |
| Barium Sulfate (C-325 6M HCL rinsed, CIMBAR) | 0 | 15 |
| NaF (1100 ppm) | 0.234 | 0.234 |
| SAPP (Sodium Acid Pyrophosphate, Prayon Inc) | 0.3 | 0.3 |

TABLE 8B-continued

Components of Formulations A and B.

| Material (Wt %) | Formula A | Formula B |
| --- | --- | --- |
| Disodium phosphate | 0.2 | 0.2 |
| Phosphoric Acid (estimate) | 0.2 | 0.2 |
| Sucralose | 0.250 | 0.250 |
| DX-18 Flavor | 1.5 | 1.5 |
| $H_2O_2$ (35% solution) | 8.570 | 8.570 |
| Total: | 100 | 100 |
| Target pH (via Phosphoric acid) | 4.5 | 4.5 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition comprising:
   (a) an effective amount of a polishing agent wherein the polishing agent comprises barium sulfate particles, wherein the particles consist essentially of at least 98.5% of barium sulfate by weight of the particle, strontium sulfate, iron(III) oxide, silicon dioxide, calcium oxide, aluminum oxide, and the particles are substantially free of calcium carbonate and the particles are free of a coating comprising citric acid salts; and
   (b) an orally acceptable carrier; and
   (c) a fluoride ion source wherein the fluoride ion source is stannous fluoride.

2. The composition of claim 1, wherein the particles have a median particle size from 8 microns to 12 microns.

3. The composition of claim 1, wherein the composition contains 0.1% to 30% barium sulfate particles by weight of the composition.

4. The composition of claim 3, wherein the composition further comprises from 0.0025% to 2% of a fluoride ion source by weight of the composition.

5. The composition of claim 1, wherein the composition further comprises 0.01% to 10% hydrogen peroxide by weight of the composition.

6. The composition of claim 3, wherein the composition further comprising an effective amount of peroxide.

7. The composition of claim 6, wherein the peroxide comprises from 0.1% to 10% by weight of the composition, and wherein the peroxide is selected from the group consisting of hydrogen peroxide, calcium peroxide, sodium peroxide, carbamide peroxide, urea peroxide, sodium percarbonate and mixtures thereof.

8. An oral care composition comprising:
   a) an effective amount of a polishing agent wherein the polishing agent comprises barium sulfate particles, wherein the particles consist essentially of at least 98.5% of barium sulfate by weight of the particle, strontium sulfate, iron(III) oxide, silicon dioxide, calcium oxide, aluminum oxide, and the particles are free of a coating comprising citric acid salts and the particles are substantially free of calcium carbonate, calcium cations, and magnesium cations and wherein the particles have a median particle size of about 8 microns;
   b) an orally acceptable carrier; and
   c) a fluoride ion source.

9. The composition of claim 8, comprising 0.0025% to 2% of the fluoride ion source by weight of the composition.

10. The composition of claim 8, comprising 0.1% to 10% of peroxide by weight of the composition, and wherein the peroxide is selected from the group consisting of hydrogen peroxide, calcium peroxide, sodium peroxide, carbamide peroxide, urea peroxide, sodium percarbonate and mixtures thereof.

11. A method of polishing tooth enamel comprising the step of brushing teeth with an oral care composition of claim 1.

12. A method of polishing tooth enamel comprising the step of brushing teeth with an oral care composition of claim 8.

13. The composition of claim 8, further comprising an effective amount of peroxide.

14. The composition of claim 1, wherein the barium sulfate particles are substantially free of magnesium cations.

15. The composition of claim 2, wherein the particles have a median particle size of 8 microns.

* * * * *